United States Patent [19]
Reich

[11] Patent Number: 4,846,836
[45] Date of Patent: Jul. 11, 1989

[54] ARTIFICIAL LOWER GASTROINTESTINAL VALVE

[76] Inventor: Jonathan D. Reich, 2223 NE. 203rd Ter., North Miami Beach, Fla. 33180

[21] Appl. No.: 252,759

[22] Filed: Oct. 3, 1988

[51] Int. Cl.[4] .................................................. A61F 2/02
[52] U.S. Cl. .................................... 623/11; 137/493.9; 137/846
[58] Field of Search ................. 623/11, 66; 137/493.9, 137/846, 493.8; 604/9, 10, 30, 39, 335, 247, 54

[56] References Cited

U.S. PATENT DOCUMENTS

| | | | |
|---|---|---|---|
| 3,155,110 | 11/1964 | Hoffman | 137/449.1 |
| 3,159,176 | 12/1964 | Russell | 137/493.1 |
| 4,181,145 | 1/1980 | Mitchell | 137/846 |
| 4,434,810 | 3/1984 | Atkinson | 137/846 |
| 4,436,519 | 3/1984 | O'Neill | 137/847 |
| 4,524,805 | 6/1985 | Hoffman | 137/846 |
| 4,623,348 | 11/1986 | Feit | 623/66 |
| 4,676,802 | 6/1987 | Tofield | 623/66 |
| 4,735,607 | 4/1988 | Keith | 604/247 |

Primary Examiner—Richard J. Apley
Assistant Examiner—James Prizant
Attorney, Agent, or Firm—Robert M. Schwartz; Edward I. Mates

[57] ABSTRACT

A bi-directional valve constructed and arranged for insertion into the esophagus in the vicinity of its lower gastroespohageal sphincter for permanent installation comprises an outer cylindrical housing that engages the inner wall of the esophagus and suspends a flexible conically or pyramidally shaped body having an open base facing the proximal (upper) end of the esophagus, a converging wall housing an upper open portion closable by an upper valve and a rounded apex having a lower slot valve facing the distal (lower) end of the esophagus.

16 Claims, 2 Drawing Sheets

ARTIFICIAL LOWER GASTROINTESTINAL VALVE

BACKGROUND OF THE INVENTION

1. Field of the Invention

This invention relates to a bi-directional valve constructed and arranged for non-surgical insertion within the fundus of an esophagus in the vicinity of its lower gastroesophageal sphincter for permanent installation therein without requiring surgery to open the esophagus to attach said bi-directional valve thereto, thereby avoiding the need for antacid medicines or other surgery.

2. Introduction of the Problem of GR Disease

Gastroesophageal Reflux Disease (or Reflux Esophagitis) is a disease which results from an improperly functioning lower gastroesophageal sphincter. The lower gastroesophageal sphincter operates on a pressure differential basis; when the pressure on the esophageal side of the sphincter exceeds a certain critical value, the sphincter opens and material passes from the esophagus into the stomach. When the pressure on the gastric side of the sphincter exceeds a different critical pressure, the sphincter opens and material passes out of the stomach and into the esophagus. The pressure at which the sphincter opens varies from person to person and is difficult to measure, but manometric studies reveal that the valve opens due to pressure as little as 5 mm Hg on the esophageal side. However, a healthy valve does not open unless pressures of more than 80 mm Hg exist on the gastric side. In patients suffering from gastroesophageal reflux disease, the pressure at which the valve distends is lowered, the threshold at which reflux occurs also is not definite. However, reflux becomes likely in people with esophagitis, if lower esophagus sphincter pressure is below 7 mm Hg. Once reflux begins, inflammation of the esophagus may set in, which, in turn, weakens the sphincter. This causes a vicious cycle of reflux causing sphincter hypertension, which increases the likelihood of reflux. The sphincter gradually degenerates. The most common symptom of gastroesophageal reflux is dyspepsia, which affects around 7% of people daily, and 30–50% of people intermittently.

Dyspepsia is defined as an uncomfortable burning sensation located below the sternum, tending to move up to the neck. Dyspepsia may mimic the symptoms of a myocardial infarction or severe angina pectoris. Other symptoms of esophageal reflux include regurgitation, dysphagia, odynphagia, hemorrhage, water brash, pulmonary manifestations due to acid aspiration (including bronchitis and bronchospasms). Repairing esophageal reflux usually requires corrective surgery. Esophageal ulcers are also serious manifestations of gastroesophageal reflux disease because they are manifested by intense continuous pain and can present acute, life threatening hematemesis due to erosion into a blood vessel. Barrett's Epithelium is the replacement of normal squamous epithelium in the esophagus by columnar epithelium. Barrett's Epithelium is also serious because it can be a premalignant condition. The incidence of adenocarcinoma was found to be 10 percent.

Another important complication of esophageal reflux is stricture. Once the esophagus lining is damaged, the cells receive impulses to produce fibrous tissues and adhesion. This is the mechanism by which the esophagus heals itself. The most common clinical manifestation of stricture is dysphagia. Unlike dysphagia from non-strictured esophageal reflux, dysphagia caused by a stricture is a progressive disorder in that the size of the bolus that can pass into the stomach progressively becomes smaller. Dysphagia weakens the peristalsis of the esophagus which, in turn, makes it harder to open the valve by reducing the esophageal pressure. If a piece of food can not pass through the stricture, regurgitation will result. Stricture is a disorder particularly relevant to this invention.

A common cause of esophageal reflux is hiatal hernia. One report showed that 21% of upper gastrointestinal disorders are due to hiatal hernias. Because some patients with hiatal hernia require surgery, there is an immediate need for patients with this condition to utilize this invention.

3. Present State of the Art

A. Non-invasive State of the Art

There are a variety of different techniques designed for treatment of less serious cases of esophagitis. Changing the nocturnal posture of patients is sometimes a first step, although it has limited effectiveness. Antacids can be prescribed to modify the fluid reflux so as to reduce the pain of dyspepsia. Some antacids cause diarrhea, others cause constipation. Other prescribed treatments include calcium carbonate, Cimetidine, or other H2 blockers. The effectiveness of these treatments vary. None totally eliminate dyspepsia. They have to be taken constantly at great cost and any cessation of them causes the pain to return without modification. They may also cause liver damage or interact with other medications.

The major problem with non-invasive techniques is that they do not eliminate reflux. They may temporarily change the nature of reflux to make it less acidic, or alter the occasions of its occurrence making it easier to sleep, but reflux will still occur. They are also temporary techniques and the patients must constantly take drugs for the rest of their lives.

B. Patents Relating to this Invention

U.S. Pat. No. 3,159,176 to Russell et al, issued Dec. 1, 1964, discloses a bi-directional valve of the duck-bill type in which reverse flow is accomplished outside the body of the valve by having reverse flow pressures in excess of a predetermined value lift a flexible umbrella portion off its seat. The construction of the Russell et al valve is such that it would require modification of the emerged umbrella to avoid its dislodgement and its tendency to cause choking.

The valve in the Russell et al patent is designed for hydrostatic pressure. Esophageal pressure is dynamic. Peristalsis of the esophagus induces the valve opening pressure. The Russell valve has a long cylindrical opening which is designed to allow fluid to accumulate. This does not work with bolus, which is solid. When bolus accumulates, it begins to smell, and deprives a person of nutrition.

U.S. Pat. No. 3,657,744 to Ersek, issued Apr. 25, 1972, shows a tool that invades the wall of a blood vessel in order to expand a housing of expanded metal that supports a prosthetic member such as a heart valve. Expansion of the housing containing the prosthetic member imbeds the expanded metal housing into the walls of the blood vessel(s) within which the housing is inserted for permanent installation.

U.S. Pat. No. 3,875,928 to Angelchik, issued Apr. 8, 1975, shows a prosthesis in the form of a generally C- shaped cushion member that is large enough to prevent extension of the gastric fundus into the thoracic cavity through an enlarged esophageal hiatus. The prosthesis is wrapped around the distal end of the esophagus to prevent the stomach from sliding into the chest area through the enlarged hiatal hernia. While this patent prevents the extension of a hernia, it does not necessarily stop reflux. Furthermore, closing the opening between the esophagus and the stomach can cause the same symptoms as stricture, mainly obstruction of food which leads to dysphagia. Also, closing the stricture may also make it impossible to regurgitate, which is a dangerous situation. Other problems that may arise from the Angelchik technique include gastric ulcers, fistula formation and general surgical complications. One surgical complication is "gas bloat" syndrome which is caused by gas not being able to leave the stomach. This was reported in 15% of patients in one study. It has been reported that 20% of patients who have primary antireflux surgery require reoperation due to recurrent reflux.

U.S. Pat. No. 4,181,145 to Mitchell, issued Jan. 1, 1980, shows a two-way check valve having a valve body with an opening covered by a flexible wall in such a manner that it defines two slits. The walls of the opening are sloped in such a manner that a forward flow pressure across the opening causes forward flow through one of the slits while the second slit remains closed. Pressure in the opposite direction causes flow through the second slit in said opposite direction while the first slit remains closed. The valve of this patent is used in a disc brake assembly and does not appear to be adaptable for use within an esophageal cavity.

The Mitchell valve is designed for pneumatic pressure. It is incompatible for food bolus (a mixture of liquid and solid). The Mitchell valve contains a large surface area on which food build-up can take place. The valves 52 and 54 are set at an angle which would allow food build-up, and once the valve opens, it would jam. The membrane 68 between the two valves 52 and 54 is so thin and pliable that it would distend and/or be dissolved by the gastric acid. The Mitchell notches 76 and 80 reduce the pressure differential required to open the valves to levels difficult to control. Also, the Mitchell construction is too wide to work in the esophagus and thus, it would bend and become dislodged.

U.S. Pat. No. 4,067,414 to Funke, issued Jan. 10, 1978, shows a one-way check valve of the duckbill type located at the outlet end of a molded plastic fitting to have lubricant pressure cause the check valve to open and feed lubricant into a housing and also force the fitting radially outwardly to engage a roughened inner wall of the housing. The Funke fitting would not work in the esophagus because it is designed to accommodate hydrostatic pressure. Any solid piece of food would get stuck in the valve. Its gastric end is too thin; anyway, the area inside the valve is too small to accommodate bolus. And of course it is unidirectional. The enlarged flange would make it impossible to use the check valve within an esophagus.

U.S. Pat. No. 4,434,810 to Atkinson, issued Mar. 6, 1984, shows different embodiments of bi-directional pressure relief valves that operate to permit forward and reverse flow at different forward and reverse flow pressures. The outer diameter of the valves are slightly greater than the inner diameter of the opening within which the valve is received. Since it is necessary to slide a valve along the length of the esophagus before it reaches a desired operating position for performing the objects of this invention, the Atkinson valve would be difficult to install. The Atkinson valve is entirely incompatible for insertion into the esophagus. Its shape would cause food to collect on the flange 16 and inside the housing. This valve would induce dysphagia. Furthermore, the construction of the Atkinson valve is much more complicated than is desirable.

U.S. Pat. No. 4,436,519 to O'Neill, issued Mar. 13, 1984, shows a one-way flow valve for use with hemostasis apparatus and emphasizes a fast connect and disconnect means and an elongated rib perpendicularly oriented with respect to a slit. The apparatus is unsuitable for use as a bi-directional valve. The O'Neill valve is incompatible for the same reason as the Atkinson valve. Its shape would cause dysphagia.

U.S. Pat. No. 4,524,805 to Hoffman, issued June 25, 1985, discloses a one-way duckbill valve, which would be unsuitable, if inserted in the vicinity of the gastroesophageal junction, as a bi-directional control valve. Furthermore, the Hoffman valve as constructed is likely to allow food to accumulate at the sides of the housing leading to the possibility of dysphagia. Also, if food bolus gets stuck in the valve corners, the stuck bolus is likely to prevent the valve from operating as desired to prevent reflux. The Hoffman valve is stressed to provide some portions that are structurally weaker than other portions. The structurally weak portion can cause the Hoffman valve to distend, which could increase the critical esophageal pressure at which the valve operates, could disrupt operation of the valve and eventually lead to dysphagia. The Hoffman valve is completely flexible and can be crushed by contraction of the esophagus during peristalsis. The crushed valve structure can be passed into the stomach, can be regurgitated, and then would be susceptible of causing either dysphagia or choking. The Hoffman valve has a structure that ensures unchanging opening pressure. This esophageal pressure required to open the Hoffman valve cannot be determined for any individual patient until after the valve is inserted, and cannot be modified while the valve remains inserted without performing invasive surgery on the esophagus. The Hoffman valve has a rigid flange formed with sharp corners that can irritate the epithelial lining of the esophagus or lacerate the esophagus and cause hemorrhaging.

BRIEF DESCRIPTION OF THE INVENTION

To the best of my knowledge, this invention represents the first time a bi-directional valve has been located within an esophagus in the vicinity of the lower gastroesophageal sphincter without surgically invading the esophagus to provide control of the flow of food toward the stomach in one direction whenever a first pressure differential within the valve in the direction of the stomach exceeds an adjustable minimum that is compatible with the characteristics of a healthy patient and to control the reflux of said patient until the reverse pressure differential exceeds a minimum pressure differential exceeding the first pressure differential.

In order to achieve the objectives of this invention, namely to provide a two-way valve that is insertable within an esophagus and occupies a permanent position within the esophagus without requiring invasive surgery of the esophagus and without causing permanent harm to the esophagus and which permits the ready flow of food particles from the esophagus into the stomach (otherwise called the gastric cavity) at a pressure on the order of magnitude of that existing in a healthy person and that prevents reflux unless an opposite pressure of a size on the order of magnitude of that normally prevailing in a healthy person by providing a bi-directional valve of unitary structure comprising a flexible, smoothly surfaced, conically or pyramidally shaped body having an open base facing the proximal end of the esophagus, a rounded apex facing the distal end of the esophagus and a flexible wall converging from said open base to said rounded apex. A one-way lower slot valve is provided in the rounded apex and is constructed and arranged to be normally closed and to be open only when the pressure on said rounded apex from the proximal end exceeds that from the distal end by a predetermined amount. The converging arrangement of the walls causes food particles to move toward the one-way lower slot valve for discharge into the stomach (or gastric cavity) without providing ledges or strictures where food particles can accumulate. The conical or pyramid shaped body is supported around its open base by a reinforced cylindrically shaped housing composed of a flexible material that does not harm the esophagus. The flexible wall has a small apertured portion that is closable by a second, upper valve adjacent the open base. The second, upper valve is constructed and arranged to be normally closed and opens only when a reverse pressure exists that is at least several times greater than said predetermined amount.

In a preferred embodiment of this invention, elongated reinforcement ribs extend from the opposite sides of said slot valve along said flexible walls to diametrically opposite portions of said open base to control the pressure required to open said slot valve.

The cylindrically shaped housing of a material that does not harm the esophagus is coupled to the open base of the open pyramid or cone and, in a preferred embodiment, comprises a plurality of circumferentially spaced, elongated reinforcements extending generally axially of said cylindrically shaped housing and comprises a proximal portion of closed cylindrical configuration, a distal portion of closed cylindrical configuration axially spaced from said proximal portion and an intermediate portion comprising a series of axially spaced rings and a plurality of axially extending ribs that interconnect said proximal portion to said distal portion and to said rings.

The unitary construction of the bi-directional valve structure is inserted into the esophagus without cutting the esophagus and, when in the proper position, the closed cylinder portions of the cylindrically shaped housing may be fixed in position within the esophagus by sutures applied from outside the esophagus into the proximal and distal portions of the cylindrically shaped housing or the valve can be fixed into the esophagus without suturing or operation using the tool of the Funke U.S. Pat. No. 3,657,744, or other non-invasive surgical implantation device. The exterior surface of the housing is designed to allow tissue in growth and patency, thereby providing stability and protection against migration without suturing. The outer housing is also designed to prevent the build-up of mucus under the valve. Mucus build-up would undermine the patency of the valve.

Further benefits of this invention will be realized from a description of a preferred embodiment that follows.

BRIEF DESCRIPTION OF THE DRAWINGS

In the drawings that form part of the description of an illustrative embodiment.

DESCRIPTION OF PREFERRED EMBODIMENT

Figure 1:
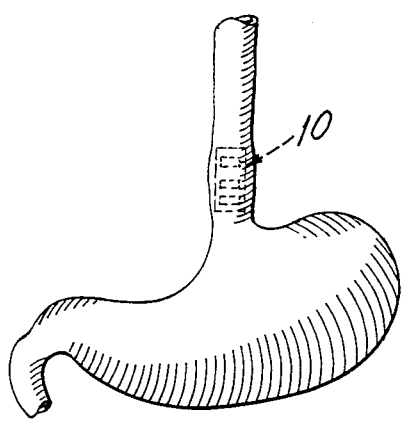
FIG. 1 is a perspective view of a portion of the digestive system of an individual, showing the preferred location of the bi-directional valve of this invention relative to the esophagus and the stomach of an individual.
Figure 2:
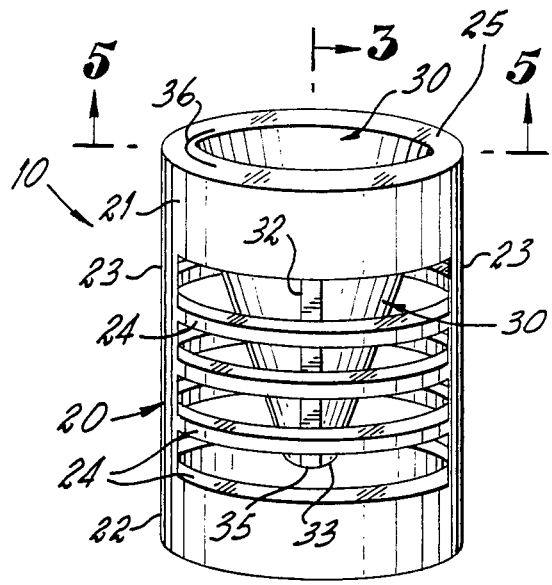
FIG. 2 is a perspective view of the bi-directional valve of FIG. 1.

A bi-directional valve 10 is shown in a desired position of emplacement within the gastro-intestinal tract of an individual in FIG. 1. The valve 10 comprises a cylindrically shaped housing 20 composed of a rubbery material that does not harm the esophagus when slid therewithin. Housing 20 comprises a proximal or upper portion 21 of closed cylindrical configuration, a distal or lower portion 22 axially spaced therefrom and an intermediate portion comprising a series of circumferentially spaced ribs 23 that interconnect the proximal portion 21, the distal portion 22 and a series of circumferential rings 24 that are axially spaced between proximal portion 21 and distal portion 22. When emplaced within the esophagus, the outer surfaces of the proximal portion 21 and the distal portion 22 engage the inner wall of the esophagus and said outer surfaces may be roughened slightly or covered with a collagen-silicone copolymer to improve the stability of the relative position between housing 20 and the esophagus. If installed surgically, sutures may be applied through the outer wall of the esophagus to attach the esophagus to the proximal portion 21 and distal portion 22. If installed non-surgically, portions 21 and 22 could be equipped with hook-like apparatus to provide installation. Ribs 23 and rings 24 are braced to enable the intermediate portion of housing 20 to expand outward, and prevent it from collapsing inward.

A circumferential connecting portion 25 extends radially inward from the upper end of proximal portion 21 to connect the cylindrically shaped housing 20 to the upper open base of an inverted conically shaped body 30. The body 30 has elongated reinforcement ribs 31 and 32 that are attached to the bottom surface of the wall of the conical body opposite the base of proximal portion 21 and extend from diametrically opposite points along the open base to a rounded apex 33 of the conical body 30. A one-way lower slot valve 35 extends along the rounded apex 33 in perpendicular relation to elongated reinforcement ribs 31 and 32 and the elongated reinforcement ribs 31 and 32 terminate at their lower ends in the center of a pair of lips that delineate slot valve 35. Slot valve 35 is constructed and arranged to open to allow downward movement of food particles and liquid nourishment through slot valve 35 in the direction of the stomach when the bi-directional valve of this invention is installed within an esophagus.

Figure 5:
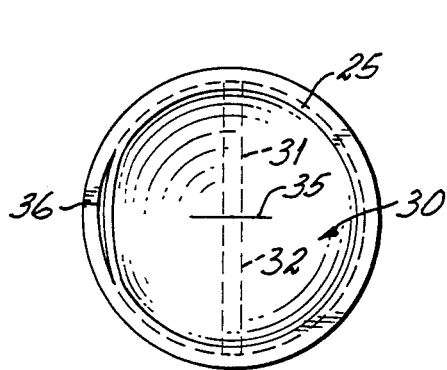
FIG. 5 is a top view of the FIG. 2 structure, showing the lower slot valve closed and an upper valve partially open.
Figure 6:
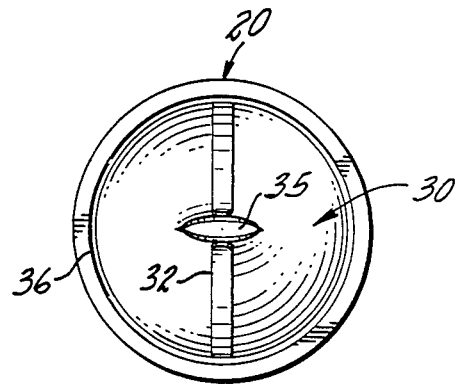
FIG. 6 is a bottom view of the FIG. 2 structure, showing the lower slot valve open and the upper valve closed.
Figure 3:
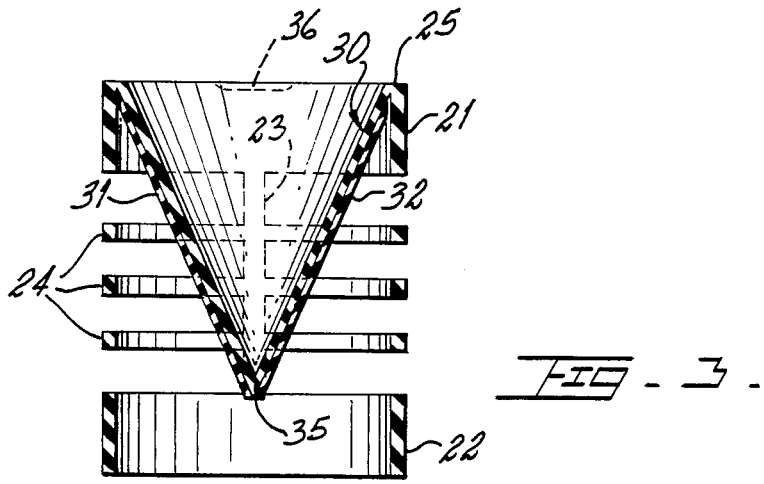
FIG. 3 is a partial vertical section along line III—III of FIG. 2 taken in a vertical plane that intersects a slot valve forming part of the bi-directional valve of FIG. 2.
Figure 4:
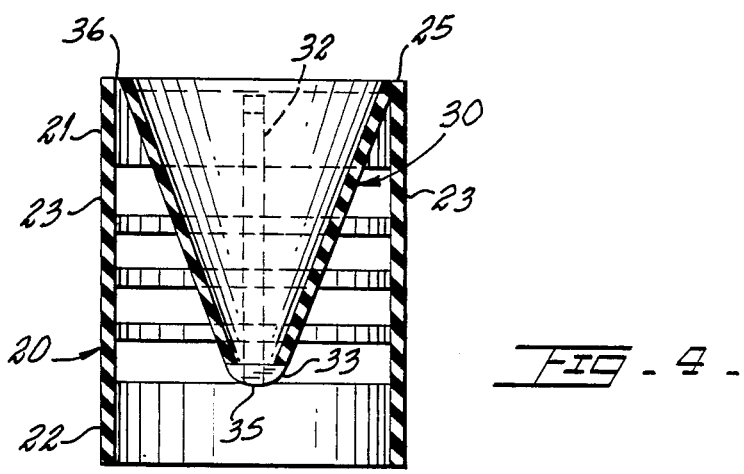
FIG. 4 is a partial vertical section taken at a right angle to FIG. 3.
Figure 7:
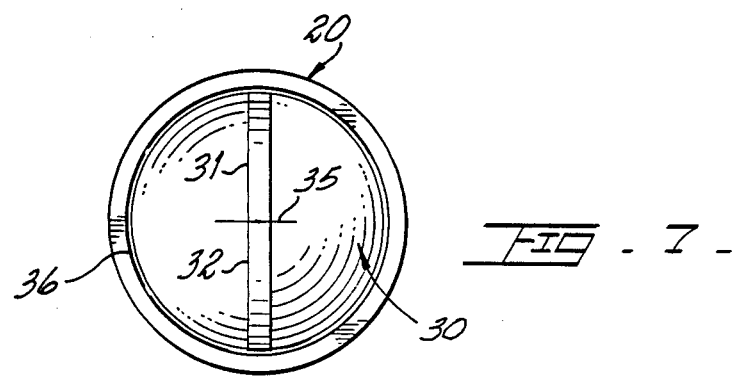
FIG. 7 is a bottom view of the FIG. 2 structure with both the upper valve and the lower slot valve closed.

A second or upper valve opening is provided between conical body 30 and the inside wall of proximal portion 21 next to the upper portion of the conical wall near the open base. The outer wall of conical body 30 and proximal portion 21 are constructed to close a second or upper valve 36. Said upper valve 36 opens normally, but is responsive to a net counter pressure opposite the direction of food flow through the esophagus to permit reflux and regurgitation when the net reverse pressure is greater than a critical gastric pressure which greatly exceeds the net downward pressure that opens the one way slot valve 35 through rounded apex 33. Second, upper valve 36 covers an opening that is short as shown in FIGS. 5 and 7, the length of the second opening extending in the general direction perpendicular to elongated reinforcement ribs 31 and 32, but transversely and vertically offset therefrom. FIG. 5 shows how second, upper valve 36 opens in response to upward pressure and FIGS. 6 and 7 show its normally closed position.

Food and drink enter the esophagus and a relatively low downward pressure slides the food particles down the conical body 30 toward the rounded apex 33. The conical body 30 and the cylindrical housing 20 are formed of a flexible rubbery material except for reinforcement ribs 31 and 32 and ribs 23 and rings 24 which are more rigid as described below. A soft silicon rubber suffices for the flexible rubbery material. A presently preferred material is a silicone rubber having a minimum specific gravity of 1.12, a tensile strength of 5.9 MPa, an elongation of 600%, a modulus of elasticity less than 10 MPa and a Shore hardness A durometer of 25 to 90.

When an individual suffers from dyspepsia or excessive reflux, and invasive surgery is not required to remove a malignancy, the bi-directional valve of this invention is assembled as a unitary structure and inserted down the gullet of an individual by sliding the valve to a desired position within the esophagus above the lower gastroesophageal sphincter. The lower slot valve 35 is constructed and arranged to be normally closed as shown in FIG. 5 and to open for downward movement in response to a downward pressure on the order of 5 millimeters of mercury. The second, upper valve 36 is constructed and arranged to remain closed, opening in between the conical wall of the conical body 30 and proximal portion 21. Valve 36 does not open thereover unless an upward pressure of more than 80 millimeters of mercury is applied by reflux to the second, upper valve. Food that has reached the stomach and mixed with gastric acids can reflux from the stomach in an upward direction toward the second, upper valve 36 and occupy a position between the conical body 30 and the esophagus below second, upper valve 36 without entering ohe upper esophagus and causing full regurgitation and/or dyspepsia until such time as the upward pressure exceeds 80 millimeters of mercury. Therefore, any instances of dyspepsia and regurgitation of refluxed food to the gullet that would occur with a weakened lower gastroesophageal sphincter is avoided by this invention. A patient with the bi-directional valve of this invention installed can be free of the discomfort of heartburn and nausea that usually exists because of a weakness of his lower gastroesophageal sphincter.

The rigidity of elongated reinforcement ribs 31 and 32 determines the pressure required to open the one way slot valve 35. Once the bi-directional valve 10 is inserted, it can be fixed in place by suturing the proximal portion 21 and the distal portion 22 through the esophagus or by non-invasive technique. The manometric pressure required to open one-way slot valve 35 can be pre-determined or changed after installation.

The esophageal pressure required to open the valve depends on the peristalsis, which differs from patient to patient. When patients have non-functioning esophageal sphincters, it is impossible to determine the necessary pressure, particularly for patients with dysphagia. Dyspshagia weakens peristalsis. Consequently, a patient who experienced dysphagia requires a valve with a much lower esophageal critical pressure.

The rigidity of reinforcement ribs 31 and 32 determines the regulatory mechanism of the slot valve 35. Altering the geometry of ribs 31 and 32 and ribs 23 and rings 24 determines their rigidity and, hence, the critical esophageal pressure. This geometry is altered by manipulating the density of the flexible rubbery material and varying the cross-sectional dimensions and area of said ribs 31 and 32 and ribs 23 and rings 24. Non-invasive laser techniques can be used to reduce the size of said ribs after the bi-directional valve has been installed without requiring its removal. Hence, it is possible to adjust the critical esophageal pressure of any patient regardless of his condition. There is no need to modify the critical gastric pressure of the bi-directional valve, because its exact value is not critical from patient to patient.

Conforming to the provisions of the patent statutes, the principle, preferred construction and mode of operation of the present invention has been explained and illustrated, and what is now considered its best embodiment has been described. However, it should be understood that, within the scope of the claimed subject matter that follows, the present invention may be practised otherwise than as specifically illustrated and described.

What is claimed is:

1. A bi-directional valve constructed and arranged for insertion within the esophagus in the vicinity of its lower gastroesophageal sphincter without surgically invading the esophagus for permanent installation therewithin comprising:
  (a) a flexible, smoothly surfaced, conically shaped body having an open base facing the proximal end of said esophagus, a rounded apex facing the distal end of said esophagus and a flexible wall extending from said open base to said rounded apex,
  (b) a first, lower one-way slot valve for said rounded apex constructed and arranged to be open only when the pressure on said rounded apex from said proximal end exceeds the pressure on said rounded apex from said distal end by a first predetermined amount and to be closed under all other pressure differential conditions on said rounded apex,
  (c) an open wall portion located on said flexible wall adjacent said open base,
  (d) a second, upper valve located in said open wall portion and constructed and arranged for said open wall portion to be open only when the pressure on said second, upper valve from said distal end exceeds the pressure on said second, upper valve from said proximal end by a second predetermined amount greater than said first predetermined amount and to close said open wall portion under all other pressure differential conditions on said second, upper valve, and (e) a cylindrical housing coupled to the open base of said conically shaped body to surround the latter and constructed and arranged of a material that does not harm said esophagus to engage said esophagus in fixed position relative thereto.

2. A bi-directional valve as in claim 1, wherein elongated reinforcement ribs extend in opposite directions from the central longitudinal portion of said slot valve along said flexible wall to diametrically opposite portions of said open base in order to control the pressure required to open said slot valve.

3. A bi-directional valve as in claim 1, wherein said flexible wall and said rounded apex are composed of a rubbery composition.

4. A bi-directional valve as in claim 3, wherein said rubbery composition has a minimum specific gravity of 1.12, a tensile strength of 5.9 MPa, an elongation of 600%, an elasticity of less than 10 MPa, and a Shore A hardness of 25 to 90.

5. A bi-directional valve as in claim 1, wherein said oneway slot valve is constructed and arranged to open when said first predetermined amount of pressure approximates the net esophageal pressure at which a normal, healthy lower gastroesophageal sphincter opens.

6. A bi-directional valve as in claim 1, wherein said cylindrical housing has a plurality of circumferentially spaced, elongated reinforcements extending generally axially of said cylindrically shaped housing.

7. A bi-directional valve as in claim 1, wherein said cylindrical housing has a proximal portion of closed cylindrical configuration, a distal portion of closed cylindrical configuration spaced axially from said proximal portion and an intermediate portion comprising a series of axially spaced rings intermediate said proximal portion and said distal portion and a plurality of circumferentially spaced, axially extending ribs interconnecting said proximal portion and said distal portion to one another and to said rings.

8. A bi-directional valve as claim 6, wherein the reinforcement ribs are constructed of a material whose rigidity can be altered by application of laser light.

9. A bi-directional valve as in claim 1, wherein said second, upper valve is constructed and arranged to open from said open wall portion only when said second predetermined amount of pressure differential on said second, upper valve is greater from said distal end than that from said proximal end by an amount on the order of one that causes reflux in a person having a normal, healthy gastroesophegal sphincter.

10. A bi-directional valve as in claim 6, wherein said second, upper valve occupies a small portion of the area of said open wall portion not exceeding 20% of said area.

11. A bi-directional valve as in claim 7, wherein said proximal portion and said distal portion have outer surfaces of roughened configuration.

12. A bi-directional valve as in claim 7, wherein said proximal portion and said distal portion are coupled to said esophagus by sutures.

13. A bi-directional valve as in claim 7, wherein said proximal portion and distal portion are adapted to be coupled to said esophagus by a non-invasive technique.

14. A bi-directional valve as in claim 1, wherein said cylindrical housing has an outer surface of roughened configuration.

15. A bi-directional valve as in claim 1, wherein said cylindrical housing is covered with a collagen-silicone copolymer.

16. A bi-directional valve as in claim 1, wherein said cylindrical housing is adapted to be coupled to said esophagus by sutures.

* * * * *